United States Patent [19]

Tanaka et al.

[11] 4,123,329

[45] Oct. 31, 1978

[54] PROCESS FOR PRODUCING L-LYSINE BY FERMENTATION

[75] Inventors: Tsutomu Tanaka, Kobe; Yoshio Nakamura, Takasago; Koji Asahi, Takasago; Tadayoshi Shiraishi, Takasago; Kenji Takahara, Kakogawa, all of Japan

[73] Assignee: Kanegafuchi Kagaku Kogyo Kabushiki Kaisha, Osaka, Japan

[21] Appl. No.: 801,083

[22] Filed: May 27, 1977

[51] Int. Cl.² .............................................. C12D 13/06
[52] U.S. Cl. .................................. 195/28 R; 195/30; 195/47; 195/49
[58] Field of Search .................... 195/28 R, 30, 47, 49

[56] References Cited

U.S. PATENT DOCUMENTS

| | | | |
|---|---|---|---|
| 3,595,751 | 7/1971 | Nakayama et al. | 195/49 |
| 3,839,151 | 10/1974 | Tanaka et al. | 195/28 R |

*Primary Examiner*—Alvin E. Tanenholtz
*Attorney, Agent, or Firm*—Moonray Kojima

[57] ABSTRACT

A process for producing L-lysine by fermentation, comprising the steps of aerobically cultivating a strain having the ability to produce L-lysine and derived from Nocardia alkanoglutinousa No. 223, in a culture medium containing an assimilable carbon source and an assimilable nitrogen source, to accumulate L-lysine in the culture medium and then recovering L-lysine.

9 Claims, No Drawings

PROCESS FOR PRODUCING L-LYSINE BY FERMENTATION

BACKGROUND OF THE INVENTION

This invention relates to a process for producing L-lysine by fermentation, and more particularly to such a process wherein a bacterium belonging to the genus Nocardia is aerobically cultivated in a culture medium, and L-lysine formed in the culture medium is recovered therefrom.

In the prior art, there are many processes for the production of L-lysine by fermentation utilizing bacteria of the genus Nocardia. For example, one such method uses an olefin as a carbon source (U.S. Pat. No. 3,440,141). Another such method uses ethyl alcohol (U.S. Pat. No. 3,595,751). A further example of such method uses a nutrient requiring strain in n-paraffin as a carbon source (U.S. Pat. No. 3,839,151). Also, another such method uses a strain resulting from imparting analog resistance to a nutrient requiring strain (British Patent 1,304,067). Each of these prior methods has its own advantages and disadvantages: most, however, do not produce large quantities of L-lysine. Accordingly, there is considerable room for improvement and substantial industrial effort has been and is being expended to improve the yields, as well as to reduce the cost.

SUMMARY OF THE INVENTION

The inventors have discovered a new species, namely, *Nocardia alkanoglutinousa* No. 223, which belongs to the genus Norcardia. Moreover, the inventors have discovered mutants, or derivatives thereof, which produce unexpectedly large amounts of L-lysine when cultivated in a culture medium having assimilable carbon source and assimilable nitrogen source. At least two such mutants of *Nocardia alkanoglutinousa* No. 223, have been discovered to produce such unexpectedly large amounts of L-lysine. These are *Nocardia alkanoglutinousa* No. 223-59 (on deposit at the American Type Culture Collection, Bethesda, Md., and having the number ATCC 31220) and *Nocardia alkanoglutinousa* No. 223-15 (ATCC 31221). Other strains derived from *Nocardia alkanoglutinousa* No. 223 and capable of producing L-lysine are encompassed by this invention.

A feature of the invention is the use of a strain derived from *Nocardia alkanoglutinousa* No. 223 and having the ability to produce L-lysine, in culture medium having a carbon source and a nitrogen source to accumulate L-lysine.

Another feature is the use of the specific derivative bacteria *Nocardia alkanoglutinousa* No. 223-59 (ATCC 31220) or *Nocardia alkanoglutinousa* No. 223-15 (ATCC 31221) in a culture medium for the formation and accumulation of L-lysine.

DETAILED DESCRIPTION OF PREFERRED EMBODIMENTS

The microorganism used in the invention is *Nocardia alkanoglutinousa* No. 223, a novel species of the genus Nocardia which the inventors isolated from the soil for the first time. *Nocardia alkanoglutinousa* No. 223 isolated from the soil produced a small amount of L-lysine in culture medium. However, *Nocardia alkanoglutinousa* No. 223-59 (ATCC 31220) and *Nocardia alkanoglutinousa* No. 223-15 (ATCC 31221) which are derived from the parent strain are both strains resistant to S-(2-aminoethyl)-L-cysteine (for convenience to be hereinafter abbreviated AEC) and form and accumulate unexpectedly large amounts of L-lysine in culture medium.

The novel species used in the invention, namely, *Nocardia alkanoglutinousa* No. 223 has microbiological properties shown hereinbelow. *Nocardia alkanoglutinousa* No. 223-59 (ATCC 31220) and *Nocardia alkanoglutinousa* No. 223-15 (ATCC 31221) have the same microbiological properties as those of the parent strain *Nocardia alkanoglutinousa* No. 223, except that the derivatives are AEC resistant.

(I) Morphology (1) Shape.
Early stage of cultivation: 0.8–1.0 × 4–15; straight rods or bent rod, branches observed.
Steady stage: Spheres or short rods close to spheres.
(2) Gram stain: positive
(3) Acid fast stain: negative
(4) motility: none
(5) endogenous spores: None; but the cells in the steady stage withstand heating at 80° C. for 1 hour in a physiologicalsaline solution.

(II) Cultivation Characteristics.

(1) Colony on a nutrient agar plate (cultivated at 33° C., 3 days) Circular, growing well, entire, pale pink, opaque, moist, smooth.
(2) Nutrient slant (cultivated at 33° C., 3 days) Filiform, growing well, pale pink, moist, smooth, no aerial mycelium observed.
(3) Nutrient broth (cultivated at 33° C.) Thin membrane on the surface, precipitates occured.
(4) Nutrient gelatin (stab culture). Not liquefied, growing on the surface and upper part.
(5) Litmus milk. Alkaline, no coagulation nor peptonization.

(III) Physiological Characteristics.

(1) Hydrolysis of starch: negative.
(2) Reduction of nitrates: positive.
(3) Formation of indole: negative.
(4) Formation of hydrogen sulfide: positive (by lead acetate paper)
(5) urease: negative.
(6) V.P. test: negative.
(7) Methyl red test: negative.
(8) Catalase: positive.
(9) Cellulose decomposition: negative.
(10) Nutrient requirement: none
(11) DNA decomposition: none
(12) Lysozyme sensitivity: present
(13) Decomposition of esculin: positive
(14) Penicillin (5 units/ml, disc. method); not sensitive.
(15) Assimilable as a carbon source: Fructose, glucose, mannitol, sorbitol, phenol, lactic acid, citric acid, acetamide, tyrosine, ethanol, mannose, n-alkanes, n-alkenes, dextrin, oils and fats, fatty acids, acetic acid.
(16) Formation of acids from sugars: acid formed from glucose, fructose, sorbitol, mannitol, glycerine and trehalose; no acid formation from xylose galactose, sucrose, lactose, maltose, inositol, dextrin and starch.
(17) Optimum growth temperature: 30° C. to 37° C.; growing at 10° C. to 40° C.
(18) Growth pH: 6–9
(19) Aerobic to oxygen.

(IV) Composition of the Cell Walls:

Containing DL-diaminopimelic acid, galactose and arabinose.

From an analysis of the above microbiological properties, the present strain was determined to be a strain belonging to the genus Nocardia. *Nocardia coralliana* and *Nocardia* sp. No. 258 are relatively similar to the present strain, but the following differences were observed.

|  | *Nocardia coralliana* | *Nocardia* sp. No. 258 | *Nocardia alkanoglutinousa* No. 223 |
|---|---|---|---|
| Urease | Not described | positive | negative |
| Formation of acods from sugars | | | |
| glucose | + | − | + |
| maltose | + | + | − |
| glycerine | + | − | + |
| Penicillin sensitivity | present | not described | none |

It is clear from the above table that *Nocardia alkanoglutinousa* No. 223 is not identical with any of the known strains of the genus Nocardia. Thus, *Nocardia alkanoglutinousa* No. 223 was identified as a novel strain of the genus Nocardia.

L-lysine producing strains, such as *Nocardia alkanoglutinousa* No. 223-59 (ATCC 31220) and *Nocardia alkanoglutinousa* No. 223-15 (ATCC 31221), are derived from *Nocardia alkanoglutinousa* No. 223 by a conventional mutation method. *Nocardia alkanoglutinousa* No. 223 is a so-called AEC sensitive strain whose growth is inhibited by AEC in a concentration of 0.4 g/liter. By a mutation treatment of other strains can be derived from *Nocardia alkanoglutinous* No. 223 which are AEC resistant and whose growth is not inhibited by AEC in a concentration of 0.4 g/liter. Further mutation treatment of AEC resistant strains of *Nocardia alkanoglutinousa* No. 223 produce other strains resistant to amino acids such as threonine or methionine or amino acid analogs such as alpha-amino-beta-hydroxy-valeric acid, alpha-amino-butyric acid or alpha-ketobutyric acid, or strains sensitive to such amino acids or analogs. These mutant strains also include those having superior L-lysine producibility. Among these AEC resistant strains, the inventors have discovered that *Nocardia alkanoglutinousa* No. 223-59 (ATCC 31220) and *Nocardia alkanoglutinousa* No. 223-15 (ATCC 31221) produce unexpectedly large amounts of L-lysine. These AEC resistant strains do not require threonine, methionine, leucine or iso-leucine. Therefore, advantageously these novel strains do not require the culture media which contain such expensive materials.

The term "AEC resistant strain", as used herein, denotes a bacterium belonging to the genus Nocardia whose growth is not inhibited by AEC in a concentration of 0.4 g/liter.

Useful carbon sources which may be used in the culture media, include, for example, carbohydrates such as glucose, fructose; a hydrolysis product of molasses or starch; organic acids such as acetic acid or citric acid; alcohols such as ethanol; animal oils and fats; vegetable oils and fats; fatty acids; n-alkanes containing 10 to 30 carbons; and hydrocarbons such as kerosene or crude oils. Examples of a nitrogen source which may be added to the culture media are ammonium acetate, ammonium sulfate, ammonium chloride, ammonium nitrate, ammonia water, amino acids, amino acid mixtures, yeast extract, peptone and meat extract. As required, inorganic salts such as phosphates, magnesium salts, calcium salts, potassium salts, sodium salts, iron salts, manganese salts, and zinc salts, and traces of other metals may be added to the culture medium. These aforementioned components of the fermentation medium may be added to the medium before sterilization or may be added to the medium in divided portions during the fermentation.

Cultivation is carried out with shaking, or with aeration and stirring, and at a pH of from 6 to 9, preferably 6 to 8, and at a temperature of 20° to 40° C., preferably 27 to 37° C. After the completion of cultivation, the culture broth has high viscosity and is sometimes difficult to filter by ordinary filtering methods. Its filterability can be improved by adding a mineral acid to adjust the pH to 1–3, or by adding an alkali to adjust the pH to at least 9, and then heating the culture broth to 80° C. or more for at least 5 minutes.

L-lysine is recovered from the filtrate in a customary manner. Specifically, the filtrate is passed through an ion-exchange resin such as IR-120 or IRC-84 for adsorption of the L-lysine, then washed with water, and then eluted with an ammonia solution. The eluate is concentrated, neutralized with concentrated hydrochloric acid, and dried to easily obtain L-lysine hydrochloride of high purity. The amount of L-lysine produced was measured by a bioassay method using a mutant strain of Escherichia coli or by using an amino acid analyzer.

The following Examples are set forth to illustrate the invention. The Examples are intended only to be illustrative and are not to be construed in any limiting manner of this invention.

EXAMPLE 1

One loopful of cells was taken from a bouillon slant culture of each of *Nocardia alkanoglutinousa* No. 223-59 (ATCC 31220) and *Nocardia alkanoglutinousa* No. 223-15 (ATCC 31221) (cultivated at 33° C. for one day), and inoculated into a large sized test tube containing 10 ml of a lysine producing culture medium having the composition set forth hereinbelow. Then, it was cultivated with shaking, at 33° C. for one day. One milliliter of the resulting culture broth was inoculated into a 500 ml Sakaguchi flask containing 30 ml of the same lysine producing culture medium, and cultivated with shaking at 33° C. for 5 days.

Composition of the L-lysine producing culture medium:

| | |
|---|---|
| n-Alkane ($C_{14}$–$C_{18}$) | 50.0 g |
| Ammonium Sulfate | 40.0 g |
| $CaCO_3$ | 30.0 g |
| $K_2HPO_4$ | 0.5 g |
| $KH_2PO_4$ | 0.5 g |
| $MgSO_4 \cdot 7H_2O$ | 0.5 g |
| NaCl | 1.0 g |
| $FeSO_4 \cdot 7H_2O$ | 20.0 mg |
| $ZnSO_4 \cdot 7H_2O$ | 10.0 mg |
| $MnSO_4 \cdot 4H_2O$ | 10.0 mg |
| tap water | 940.0 ml |
| pH | 7.0 |
| 120° C | Steamed for 15 minutes. |

The amounts of L-lysine produced in the culture media (as hydrochlorides) were as follows:

| | | L-lysinehydrochloride (g/liter) |
|---|---|---|
| *Nocardia* | No. 223-59 | 19.5 |

| | | L-lysinehydrochloride (g/liter) |
|---|---|---|
| alkanoglutinousa | (ATCC 31220) | |
| Nocardia alkanoglutinousa | No. 223-15 (ATCC 31221) | 28.7 |

EXAMPLE 2

One loopful of cells was taken out from a bouillon slant culture of *Nocardia alkanoglutinousa* No. 223-59 (ATCC 31220) (cultivated at 33° C. for one day), and inoculated into a 500 ml Sakaguchi flask containing 30 ml of a culture medium having the same composition as the culture medium used in Example 1 except that corn oil (in 1 case) and fish oil (in another case) were used instead of the n-Alkane, and then cultivated with shaking. After cultivation for 5 days, L-lysine as hydrochloride was obtained in an amount of 6.6 g/liter in the corn oil containing culture medium and 6.3 g/liter in the fish oil containing culture medium.

EXAMPLE 3

One loopful of cells was taken out from a slant culture of *Nocardia alkanoglutinousa* No. 223-15 (ATCC 31221) (cultivated at 33° C. for one day), and inoculated into a 500 ml Sakaguchi flask containing 30 ml of a culture medium having the same composition as the culture medium used in Example 1 except that stearic acid (in one case) and margaric acid (in another case) were used instead of the n-Alkane, followed by shaking cultivation at 33° C. for five days. The amount of L-lysine as a hydrochloride which was accumulated was 15.3 g/liter in the stearic acid containing culture medium, and 14.4 g/liter in the margaric acid containing culture medium.

EXAMPLE 4

One loopful of cells was taken out from a bouillon slant culture of *Nocardia alkanoglutinousa* No. 223-59 (ATCC 31220), and inoculated into a 500 ml Sakaguchi flask containing 30 ml of a culture medium having the same composition as the culture medium used in Example 1, except that ethyl alcohol was used instead of the n-alkane (added in portions of less than 1%), followed by shaking cultivation at 33° C. for 5 days. L-lysine as a hydrochloride was produced in an amount of 13.0 g/liter.

EXAMPLE 5

One loopful of cells was taken out from a bouillon slant culture of *Nocardia alkanoglutinousa* No. 223-15 (ATCC 31221)(cultivated at 33° C. for one day), and inoculated in a Sakaguchi flask containing 30 ml of the same culture medium as used in Example 1, followed by shaking cultivation at 33° C. for one day. 5 ml of theresulting culture broth was inoculated into a 2 liter Sakaguchi flask containing 200 ml of the same culture medium as used in Example 1, and cultivated with shaking at 33° C. for one day. 600 ml of the culture broth was inoculated into a 30 liter jar containing 18 liters of an L-lysine producing culture medium having the composition indicated below, and cultivated at 33° C. while stirring at 400 rpm and passing air therethrough at the rate of 9 liters per minute. During the cultivation, the culture medium was neutralized to pH of 7.0 with ammonia water. After 96 hours of cultivation, L-lysine as a hydrochloride was obtained in an amount of 52.5 g/l. Concentrated sulfuric acid was added to one liter of the resulting culture broth to adjust its pH to 1.5 and was heated at 100° C. for 20 minutes and then filtered. The filtrate was passed through an ion exchange resin (IR-120, $NH_4^+$ type) for adsorption of L-lysine, washed with water, and then eluted with ammonia. The eluted fractions were concentrated, neutralized with concentrated hydrochloric acid, and dried to form 45 g of L-lysine hydrochloride having a purity of more than 98%.

The composition of the L-lysine producing culture medium used in the Example 5 was as follows:

| | |
|---|---|
| n-Alkane ($C_{14}$-$C_{19}$) | 100.0 g |
| Ammonium sulfate | 35.0 g |
| $CaCl_2 \cdot 2H_2O$ | 1.0 g |
| NaCl | 1.0 g |
| $K_2HPO_4$ | 1.0 g |
| $KH_2PO_4$ | 1.0 g |
| $MgSO_4 \cdot 7H_2O$ | 0.5 g |
| $FeSO_4 \cdot 7H_2O$ | 100.0 mg |
| $MnSO_4 \cdot 4H_2O$ | 20.0 mg |
| $ZnSO_4 \cdot 7H_2O$ | 20.0 mg |
| Tap water | 870.0 ml |
| pH | 7.0 |
| 120° C | Steamed for 15 minutes |

EXAMPLE 6

Calcium hydroxide was added to one liter of the culture broth obtained in Example 5 to adjust its pH to 11. The culture broth was then heated at 100° C. for 30 minutes, aerated at the flow rate of 1 v.v.m. for 2 hours, and then concentrated sulfuric acid was added to adjust the pH to 5.0, followed by filtration. The filtrate was passed through an ion exchange resin (IR-120, $NH_4^+$ type) for adsorption of L-lysine, washed with water, and then eluted with ammonia. the eluted fractions were concentrated, neutralized with concentrated hydrochloric acid, and dried to produce 46 g of L-lysine hydrochloride having a purity of more than 98%.

EXAMPLE 7

One loopful of cells was taken from a bouillon slant culture of *Nocardia alkanoglutinousa* No. 223-15 (ATCC 31221) (cultivated at 33° C. for one day), and inoculated into a 500 ml Sakaguchi flask containing 30 ml of a culture medium having the same composition as the culture medium used in Example 1, except that glucose was used instead of the n-alkane, followed by shaking cultivation at 3320 C. for 4 days. The amount of L-lysine accumulated in the culture medium was 0.5 g/liter as a hydrochloride.

EXAMPLE 8

One loopful of cells was taken out from a bouillon slant culture of *Nocardia alkanoglutinousa* No. 223-15 (ATCC 31221) (cultivated at 33° C. for one day), and inoculated into a 500 ml Sakaguchi flask containing 30 ml of a culture medium having the same composition as the culture medium used in Example 1, except that acetic acid was used instead of the n-alkane (added in portions of less than 0.5%) followed by shaking cultivation at 33° C. for 4 days. The amount of L-lysine as hydrochloride accumulated in the culture medium was 2.2 g/liter.

The foregoing description is illustrative of the principles of the invention. Numerous variations and modifications thereof would be apparent to the worker skilled in the art. All such variations and modifications are to be considered to be within the spirit and scope of the invention.

What we claim is:

1. Process for producing L-lysine comprising aerobically culturing a microorganism belonging to the species *Nocardia alkanoglutinousa* and having the morphological, culturing and physiological properties of *Nocardia alkanoglutinousa* No. 223-59 (ATCC 31220) or *Nocardia alkanoglutinousa* No. 223-15 (ATCC 31221) in a medium and recovering L-lysine accumulated in said medium.

2. The process of claim 1, wherein said carbon source is selected from the group consisting of n-alkane containing 10 to 30 carbon atoms, kerosene containing n-alkane, and crude oil containing n-alkane.

3. The process of claim 1 wherein said carbon source is selected from the group consisting of animal oil, animal fat, vegetable oil and vegetable fat.

4. The process of claim 1, wherein said carbon source is a fatty acid.

5. The process of claim 1, wherein said carbon source is ethyl alcohol.

6. The process of claim 1, wherein said carbon source is selected from the group consisting of glucose, fructose, a hydrolysis product of molasses, and a hydrolysis product of starch.

7. The process of claim 1, wherein said carbon source is acetic acid or citric acid.

8. The process of claim 1, wherein after cultivation, said culture medium is adjusted to a pH of 1 to 3, and heated at a temperature of at least 80° C. for at least five minutes.

9. The process of claim 1, wherein after cultivation said culture medium is adjusted to a pH of at least 9, and heated at a temperature of at least 80° C. for at least five minutes.

* * * * *